ST. AUGUSTINE GRASS
Filed Oct. 2, 1972 2 Sheets-Sheet 1
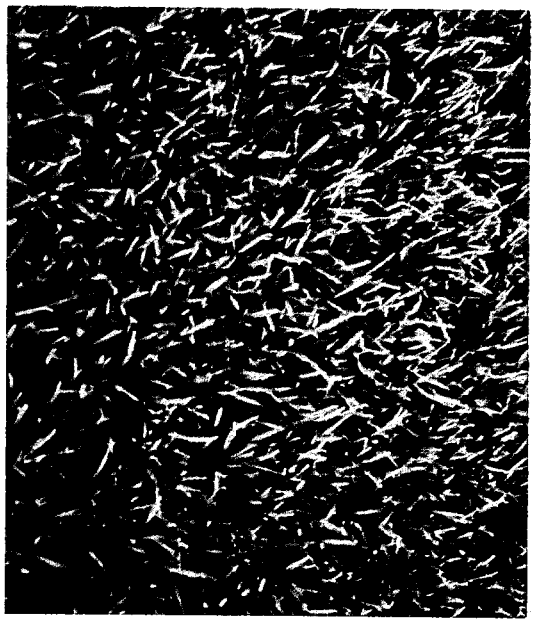
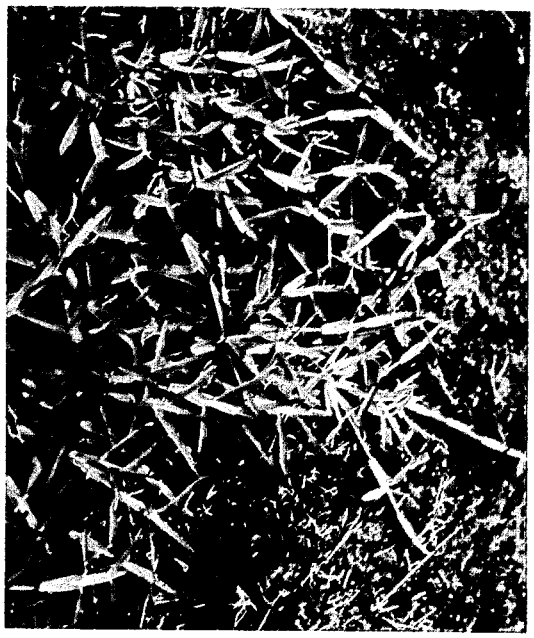
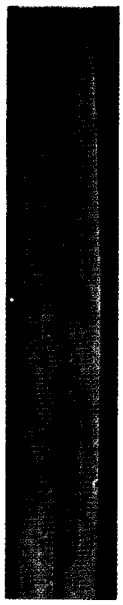

ST. AUGUSTINE GRASS
Filed Oct. 2, 1972
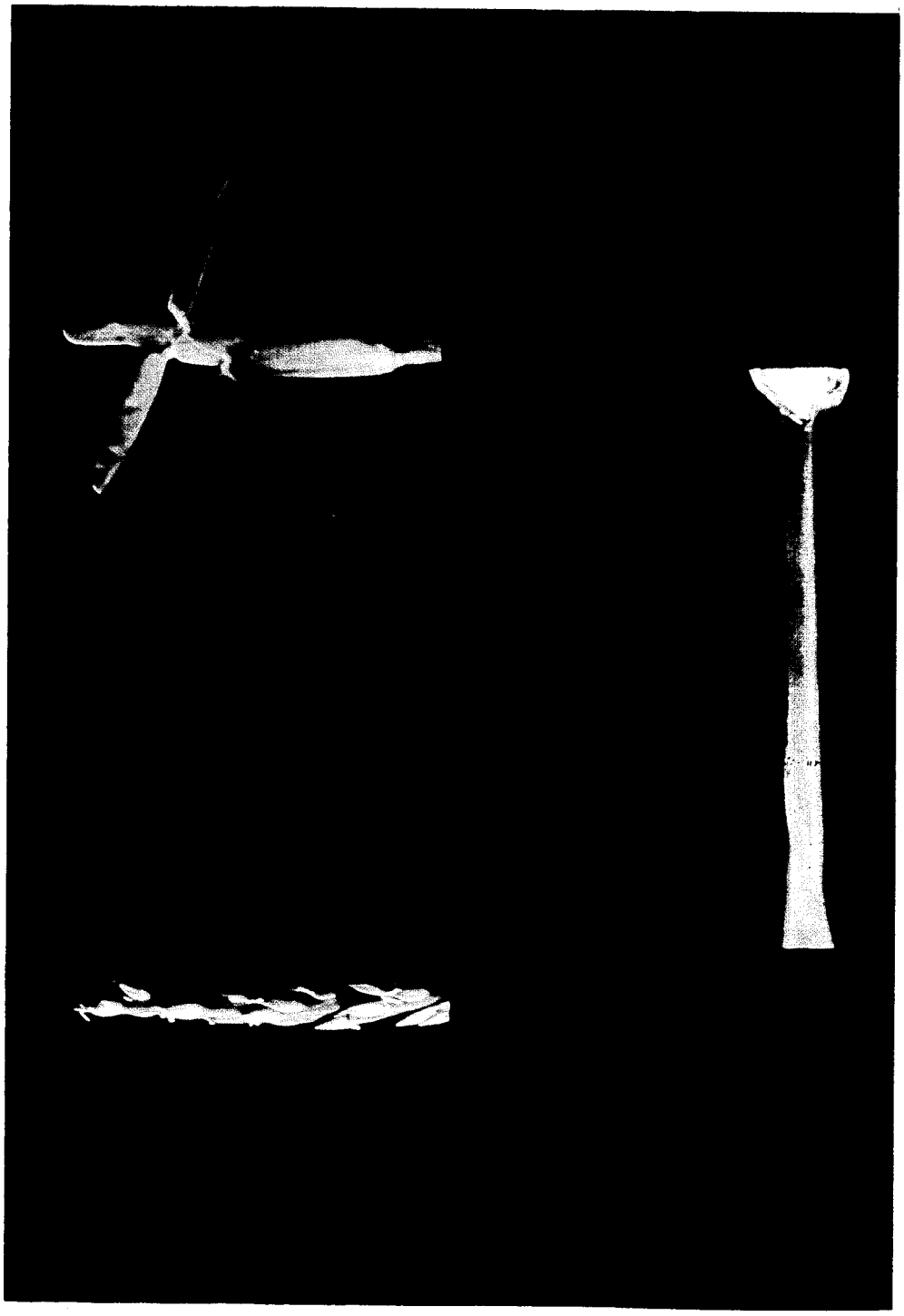

United States Patent Office

Plant Pat. 3,491
Patented Feb. 26, 1974

3,491
ST. AUGUSTINE GRASS

Curran L. Garrett, Ingleside, and Joseph T. Mahoney, Corpus Christi, Tex., assignors to Curran L. Garrett, Ingleside, Tex.

Filed Oct. 2, 1972, Ser. No. 293,921
Int. Cl. A01h 5/00
U.S. Cl. Plt.—88 1 Claim The present invention relates to a new and distinct variety of St. Augustine grass which was discovered by us as a newly found seedling of unknown parentage which originated in the cultivated lawn growing on property owned by one of us and located in Corpus Christi, Tex.

At the time of our discovery, we were jointly engaged in a study of the lawn at the home of one of us in Corpus Christi, Tex., which was largely dried up and dead. During this study, our attention was attracted to a small patch of grass in a part of this lawn which appeared to be thriving. Close inspection of this small patch showed that the plants appeared to be somewhat different in a number of respects from other St. Augustine varieties, and the other of us immediately recognized the potential significance of its value as a superior variety, due to his long experience in the care and treatment of lawn grasses, and more particularly St. Augustine grasses. We, therefore, carefully preserved the original small patch and promptly took stolons therefrom, some of which were transplanted to other areas of the lawn, and elsewhere under our control and others of which were set in small pots for continued observations and tests. The original plants and their progeny grew rapidly and have continued to thrive over the years without any evidence of virus infection therein. For identification purposes, our new variety has been designated as #4875. Although its derivation is uncertain, we believe that it originated as a seed mutation.

St. Augustine grass has been and is extensively grown in the southern regions of the United States, particularly along the Gulf Coast. Prior to our discovery aforesaid beginning in the early 1960's, the St. Augustine lawn grasses in Corpus Christi began to yellow and die. After several years of extensive efforts to solve this problem by treatments of the grasses with many types of fertilizers, insecticides, fungicides and other materials, no successful solution of the problem had been found. Research departments of some agricultural colleges began work on the problem, and in the late 1960's, they diagnosed the same as a new virus disease which was named St. Augustine decline virus (abbreviated SADV). In the meantime, SADV had grown to a devasting extent all along the Gulf Coast of Texas, as far north as Fort Worth, and along the Rio Grande River from the coast to Del Rio. In Corpus Christi alone, 80% of the lawns were affected with SADV in 1969, repersenting a potential loss of some 17 million dollars to home owners. It was estimated that within about 3 years, this disease would probably extend to Florida, and accordingly, efforts to solve the problem were intensified, in which we took part with the assistance of some of the agricultural colleges, particularly Texas A & M University.

All available types of St. Augustine grasses, including our own, have been carefully screened and tested for their susceptibility to SADV. These tests have included field tests, as well as mechanical innoculations utilizing standard inoculation procedures. Of all these grasses, our new variety has been outstanding, as evidenced by the following unique combination of characteristics which distinguish our new grass from all other St. Augustine varieties of which we are aware:

(1) Superior tolerance to St. Augustine decline virus (SADV), with no evidence of any susceptibility thereto in either field trials or in inoculation tests;
(2) A pleasing attractiveness for lawn plantings;
(3) An ability to be easily propagated from stolons;
(4) A relatively fast growing habit, although somewhat slower than Texas common;
(5) Good hardiness to temperatures as low as 13° F.;
(6) An exceptionally long internode length; and
(7) Distinctive purple stigmas, with white filaments toward the base.

Asexual reproduction of our new St. Augustine grass, as performed by us in Corpus Christi, Tex. from stolons planted in pots and in outdoor field plants, as well as in test plantings performed by Texas A & M University, shows that the foregoing characteristics and distinctions are established and come true through succeeding propagations.

The accompanying drawings show a typical turf plot and plants of our new variety, as well as a typical specimen leaf blade, stem, stolon, bud, spikelet and stigma on a somewhat larger scale than the view of the turf, as depicted in color as nearly true as it is reasonably possible to make the same in color illustrations of this character.

The following is a detailed description of our new variety of St. Augustine grass, with color terminology in accordance with ISCC-NBS Centroid Color Charts, except where general color terms of ordinary dictionary significance are obvious:

Growth habit: Upright stoloniferoun; medium fast growing.
Culms: Branching; highly compressed.
*Flowering shoots.*—About 33 cm. tall.
Stolons: Large; oval shaped.
*Color.*—Dark Gray Red, Color No. 20, NBS, Circular No. 553.
Internodes: Oval shaped; about 3.18 cm. x 2.38 mm. in cross section and average about 47.63 mm. in length.
Leaf blade: Leaves folded in the bud.
*Length.*—Average about 28.1 cm.
*Width.*—Averages about 7.14 mm.
*Color.*—Medium Olive Green, No. 125, NBS Circular No. 553.
*Veination.*—Obscure except the mid-rib which is prominent on the underside.
*Collar.*—Wide at margins; narrow at midrib; auricles absent; outer edge of collar has numerous long hairs averaging about 2.10 mm. long; collar continuous white color.
Ligule: With continuous fringe of hairs about 0.2 mm. long.
Inflorescence: Long fleshy racemes, with spikelets embedded.
Racemes: Average about 7.15 cm. long.
Spikelets: About 4.65 mm. long.
First glume: Average about 1.0 mm. long.
Second glume: About 4.10 mm. long.
Palea: About 4.0 mm. long.
Stigma:
*Color.*—Basically purple, with some feathery white filaments toward the base.
Seeds: Plant is sterile and has never produced seed either through self-or cross-pollination.

COMPARATIVE TABLE

| Variety | Growth habit | Leaf color | Leaf length, cm. | Leaf width, mm. |
|---|---|---|---|---|
| (1) #4875 | Upright | Medium olive green. | 13.86 | 7.14 |
| (2) Floratam | do | Bluish | 10.0 | [1] 0.9 |
| (3) Scotts #1081 | Low-growing | Moderate olive green | <6.0 | 7.0–7.5 |

| | Internode Color | Internode length, mm. | Internode diameter, mm. | Flower shoot height, cm. | Raceme, cm. |
|---|---|---|---|---|---|
| (1) #4875 | Dark gray red | 47.62 | 3.18 x 2.38 | 33 | 7.15 |
| (2) Floratam | Dark red | [1] 7.62 | | 30–45 | |
| (3) Scotts #1081 | | | | 5–15 | 5–10 |

| | Spikelets, mm. | First glume, mm. | Second glume, mm. | Palea, mm. | Lemma, mm. | Stigma color |
|---|---|---|---|---|---|---|
| (1) #4875 | 4.65 | 1.0 | 4.10 | 3.9 | 4.0 | Purple with white filaments toward base. |
| (2) Floratam | | | | | | Purple. |
| (3) Scotts -1081 | 3.2–3.3 | 1.07–1.11 | 3.0–3.06 | 2.96–3.02 | 3.09–3.39 | Do. |

[1] Centimeters.

Floratam is an unpatented St. Augustine grass jointly released by Texas A & M University and the University of Florida, while Scott's #1081 is a patented variety which is the subject of Plant Pat. No. 2,863.

General observations: It will be apparent from the foregoing comparative table that "Floratam" is a much coarser grass than our new variety #4875, while Scott's #1081 is a much finer grass and is less resistant to cold weather.

We claim:

1. A new and distinct variety of St. Augustine grass, substantially as herein shown and described, characterized particularly as to novelty by the unique combination of superior tolerance to St. Augustine decline virus (SADV), with no evidence of any susceptibility thereto in either field trials or in inoculation tests, a pleasing attractiveness for lawn plantings, an ability to be easily propagated from stolons, a relatively fast growing habit, although somewhat slower than Texas common, good hardiness to temperatures as low as 13° F., an exceptionally long internode length, and distinctive purpose stigmas, with white filaments toward the base.

No references cited.

ROBERT E. BAGWILL, Primary Examiner

UNITED STATES PATENT OFFICE

CERTIFICATE OF CORRECTION

Plant
Patent No. 3491 Dated February 26, 1974

Inventor(s) Curran L. Garrett and Joseph T. Mahoney

It is certified that error appears in the above-identified patent and that said Letters Patent are hereby corrected as shown below:

Column 4, line 29 (next to last line of claim 1), change "purpose" to --purple--.

Signed and sealed this 2nd day of July 1974.

(SEAL)
Attest:

EDWARD M.FLETCHER,JR.
Attesting Officer

C. MARSHALL DANN
Commissioner of Patents

USCOMM-DC 60376-P69
☆ U.S. GOVERNMENT PRINTING OFFICE : 1969 O—366-334.